United States Patent [19]

Logan

[11] 4,064,880

[45] Dec. 27, 1977

[54] SANITARY TUBULAR NAPKIN FOR MALES

[76] Inventor: Dexter J. Logan, 1215 W. Farlington St., W. Covina, Calif. 91790

[21] Appl. No.: 721,099

[22] Filed: Sept. 7, 1976

[51] Int. Cl.² .............................................. A61F 5/42
[52] U.S. Cl. ................................ 128/294; 128/132 R; 128/157; 221/47
[58] Field of Search ................... 128/294, 295, 132 R, 128/157; 221/45, 47; 206/362, 363, DIG. 7

[56] References Cited

U.S. PATENT DOCUMENTS

| | | | |
|---|---|---|---|
| 2,604,092 | 7/1952 | Brown et al. | 128/294 |
| 3,018,484 | 1/1962 | Koehn | 128/132 R |
| 3,934,582 | 1/1976 | Gorrie | 128/157 |
| 3,939,836 | 2/1976 | Tune | 128/284 |
| 3,958,574 | 5/1976 | Rohr | 128/295 |

FOREIGN PATENT DOCUMENTS

| | | | |
|---|---|---|---|
| 60,617 | 2/1948 | Netherlands | 221/47 |
| 107,947 | 7/1917 | United Kingdom | 221/47 |

Primary Examiner—Stephen C. Pellegrino
Assistant Examiner—Henry S. Layton
Attorney, Agent, or Firm—J. C. Baisch

[57] ABSTRACT

The present invention relates to a sanitary tubular napkin for male hygiene; and is directed to urinal or toilet-towl disposable napkins that comprise an absorbent material. The disclosed napkins are formed into a set of napkins that are joined together; and the set of napkins is placed in a dispenser. A separating means permits the removal of one napkin, and positions the subsequent napkin in a position for subsequent removal.

1 Claim, 6 Drawing Figures

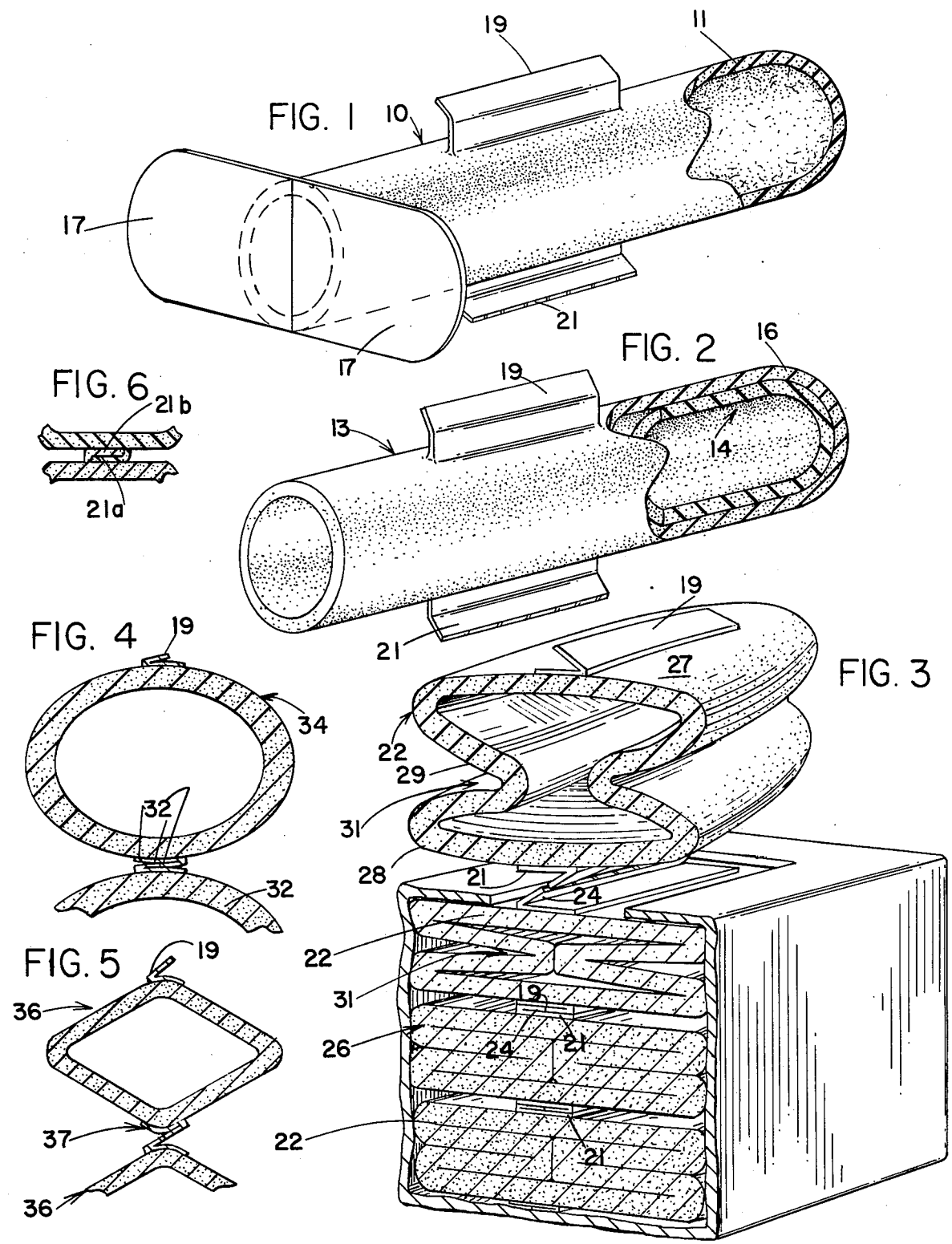

SANITARY TUBULAR NAPKIN FOR MALES

BACKGROUND OF THE INVENTION

Field of the Invention

It is well known that there is a wide need for sanitary napkins for male hygiene; the reason for this need includes: the protection of hands and clothing during expelling of post-urinary drip, involuntary discharge of semen, post prostatic surgery, loss of sphincter muscle control, kidney disorders, and the like.

OBJECTS AND ADVANTAGES OF THE INVENTION

It is a principal objective of the present invention to provide an improved sanitary napkin for male hygiene.

It is another object of the invention to provide a sanitary napkin adapted to envelop the male genital organ.

It is still another objective of the present invention to provide an improved male-hygiene sanitary napkin that is urinal or toilet-bowl disposable.

It is a further objective of the present invention to provide an improved male-hygiene sanitary napkin that may be formed into a set of napkins.

It is a still further objective of the present invention to provide an improved male-hygiene sanitary napkin that may be formed into a set of napkins that may be connected for insertion into a dispenser.

BRIEF DESCRIPTION OF THE DRAWINGS

The attainment of these objectives and others will be realized from the following specification, taken in conjunction with the drawings, of which:

FIG. 1 shows one type of napkin;

FIG. 2 shows another type of napkin;

FIG. 3 shows a partially-exploded, partially-cutaway view of compacted set of napkins positioned in a dispenser;

FIG. 4 shows a cutaway view of different form of napkin for use in a dispenser;

FIG. 5 shows a cutaway view of still another form of napkin for use in a dispenser;

FIG. 6 is a fragmentary sectional view wherein the tabs are interfolded or overlapped for positioning the tab of the next napkin by pulling the tab through the exit slot opening in the dispenser.

SYNOPSIS

Broadly speaking, the present invention discloses a tubular napkin having an absorbent portion. A plurality of napkins are separably joined together to form a tandem set of napkins that may be positioned in a dispenser. The joining means may take the form of a separating strip — such as a tear strip or a group of breakaway adhesive spots. Alternatively, the sanitary napkins can be separably connected by interfolding or overlapping the pull tabs on each adjacent compacted napkin.

DISCLOSURE

FIG. 1 illustrates a partially cutaway view of a tubular napkin 10 comprising an absorbent layer 11 of material such as paper mat, a form of absorbent tissue paper or the like — material such as these forming an inexpensive napkin that may be urinal or toilet-bowl disposable. As illustrated in FIG. 2, napkin 13 may — if desired — comprise an inner absorbent pocket 14 and an outer tube 16 of reinforcing material such as paper-mesh, a form of absorbent paper with threads in it, or the like — reinforcing materials such as these also forming an inexpensive napkin that may be urinal or toilet-bowl disposable.

Napkins 10 and 13 may have positioning flaps such as 17; these flaps being coated with a pressure sensitive adhesive.

It will be noted that the illustrated napkins have a centrally located removal tab 19 on the upper portion of the napkin; and these tabs may be either affixed-to, or integral-with, the napkin — and the terms "affixed" is therefore to be construed as including a tab that is either attached or integral-with the napkin structure.

It will also be noted that the napkin illustrated in FIGS. 1 and 2 also have a centrally located retaining element 21 on the lower portion of the napkin; and that this retaining element 21 is similarly affixed to the napkin.

FIG. 3 is a partially-exploded partially-cutaway view that shows a plurality of napkin 22 joined together to form a tandem set of napkins; the tandem set being formed by suitably joining each removal tab 19 to the retaining element 21 of a subsequent napkin. The joining means may comprise any convenient arrangement — such as a perforated tear strip 24 which comprises a tear line along which a tear takes place when one napkin is pulled away from the next napkin. With this arrangement the perforations extend longitudinally midway between the napkin.

Alternatively, the joining means may comprise spots of breakaway adhesive, or the like — as will be discussed later.

As indicated in FIG. 3, the tandem set of napkins may be compacted to form a flat pack that fits into a dispenser 26.

The napkins 22 illustrated in FIG. 3 as forming the flat pack have an upper surface 27, a lower surface 28, and two side surfaces 29 that each have a longitudinal re-entrant fold 31 therein. When a napkin 22 having this re-entrant configuration is compacted, the longitudinal re-entrant fold 31 collapses as indicated; and when the removal tab is pulled, the re-entrant fold 31 opens so that the napkin 22 forms a substantially square cross-sectional configuration.

With the folded type of napkin, they may be interfolded in the dispenser so that as one napkin is removed, another is pulled into position for being grasped with the thumb and fingers and removed from the dispenser.

Alternatively, as illustrated in FIG. 4, the cross-sectional view of napkin 34 shows an oval cross-sectional configuration, and a removal tab 19; and the previously-disclosed retaining element may take the form of a few spots 32 of breakaway adhesive.

If desired, as indicated in FIG. 5, the napkin 36 of a flat pack set of napkins may have suitable removal tabs 19, retaining element 37 and a diamond shaped cross-sectional configuration.

In FIG. 6 there is shown another alternative arrangement wherein adjacent tabs, such as the lower tab 21-A of a napkin in a stack of napkins and the upper tab of the adjacent napkin are interfolded or overlapped for pulling the tab of the lower napkin through the exit slot of the dispenser when the upper napkin is pulled through said slot.

In FIG. 6, the dispenser is shown with the dispensing slot at the top. This arrangement is desirable when the dispenser is placed on a shelf or the like. The dispenser may be attached to a wall or the like with the slot at the bottom. With the tabs of the napkins interfolded, the lower napkin is removed through the slot by means of its lower tab. As the napkin is pulled downwardly through the slot of the dispenser by means of the lower tab, the tab of the adjacent napkin is pulled downwardly through said slot.

I claim:

1. A tubular sanitary napkin of the type described, comprising:

a removal-tab positioned centrally of said napkin;

said napkin being closed at one end, and being open at the other end thereof, and having an upper portion and a lower portion, wherein said removal-tab is affixed to said upper portion of said napkin;

a retaining element fixedly positioned centrally on said lower portion of said napkin;

a second napkin having an upper and a lower portion, including a removal-tab affixed to said upper portion thereof and joined to said retaining element of said lower portion of said first napkin;

joining means for joining together said tabs;

a plurality of similar napkins having their removal-tabs joined to the retaining elements of preceding napkins, and having their retaining elements joined to the removal-tabs of subsequent napkins — said plurality of napkins forming a tandem set of napkins, whereby said tandem set of napkins may be compacted to a flat pack;

and wherein said napkins have an upper surface, a lower surface, and two side surfaces;

each of said side surfaces having a longitudinal re-entrant fold therein.

* * * * *